(12) United States Patent
Pozzi et al.

(10) Patent No.: US 8,714,408 B2
(45) Date of Patent: May 6, 2014

(54) SELF-CLEANING TIP

(75) Inventors: Jacques Pozzi, Antibes (FR); Pierre Roy, Paris (FR)

(73) Assignee: Sivel, Antibes (FR)

( * ) Notice: Subject to any disclaimer, the term of this patent is extended or adjusted under 35 U.S.C. 154(b) by 124 days.

(21) Appl. No.: 13/144,755

(22) PCT Filed: Feb. 1, 2010

(86) PCT No.: PCT/FR2010/050161
§ 371 (c)(1),
(2), (4) Date: Jul. 15, 2011

(87) PCT Pub. No.: WO2010/089501
PCT Pub. Date: Aug. 12, 2010

(65) Prior Publication Data
US 2011/0278323 A1 Nov. 17, 2011

(30) Foreign Application Priority Data

Feb. 3, 2009 (FR) ..................................... 09 00433

(51) Int. Cl.
*B65D 47/40* (2006.01)
(52) U.S. Cl.
USPC ............ 222/108; 222/422; 222/571; 222/148
(58) Field of Classification Search
USPC ......... 222/571, 135, 387, 494, 148, 108, 422; 239/106
See application file for complete search history.

(56) References Cited

U.S. PATENT DOCUMENTS

| | | | |
|---|---|---|---|
| 5,238,153 A * | 8/1993 | Castillo et al. ........... | 222/189.09 |
| 5,377,880 A * | 1/1995 | Moretti ......................... | 222/207 |
| 5,492,252 A | 2/1996 | Gueret | |
| 5,971,224 A * | 10/1999 | Garibaldi ....................... | 222/207 |
| 6,053,368 A | 4/2000 | Geimer | |
| 6,082,586 A * | 7/2000 | Banks ............................. | 222/95 |

(Continued)

FOREIGN PATENT DOCUMENTS

| FR | 2638428 | 10/1988 |
|---|---|---|
| FR | 2661401 A1 | 10/1991 |

(Continued)

OTHER PUBLICATIONS

Search Report from counterpart French Application No. 0900433; Report dated Apr. 5, 2009.

(Continued)

*Primary Examiner* — Kevin P Shaver
*Assistant Examiner* — Robert Nichols, II
(74) *Attorney, Agent, or Firm* — Miller, Matthias & Hull LLP

(57) ABSTRACT

The invention relates to a device for packaging and dispensing a generally liquid or viscous product, including a container for containing the product to be packaged and dispensed in the form of clean or sterile calibrated doses or drops using a dispensing accessory including a tip, wherein the assembly of the container and the accessory includes an additional flexible and deformable chamber actuated simultaneously with the accessory and capable of either sucking the residual drop at the end of said accessory after dispensing a calibrated dose or drop, or of blowing said calibrated dose or drop without permitting the formation of a residual drop. The invention can be used for packaging and dispensing clean or sterile products, in particular doses or drops in the field of ophthalmology.

7 Claims, 4 Drawing Sheets

(56) References Cited

U.S. PATENT DOCUMENTS

| | | | |
|---|---|---|---|
| 6,336,571 B1 | 1/2002 | Chibret et al. | |
| 7,303,098 B2 * | 12/2007 | Backes | 222/212 |
| 8,360,287 B2 * | 1/2013 | Ciavarella et al. | 222/372 |
| 2008/0296320 A1 * | 12/2008 | Kang | 222/394 |
| 2008/0302828 A1 | 12/2008 | Pozzi | |
| 2009/0184136 A1 * | 7/2009 | Ciavarella | 222/190 |
| 2009/0318883 A1 | 12/2009 | Sugahara et al. | |
| 2011/0163114 A1 * | 7/2011 | Webb | 222/1 |

FOREIGN PATENT DOCUMENTS

| | | |
|---|---|---|
| FR | 2770495 | 5/1999 |
| FR | 2873358 | 7/2000 |
| FR | 0510907 | 10/2005 |
| FR | 2873358 | 1/2006 |
| JP | 2007268830 A | 10/2007 |
| WO | WO 00/13476 A3 | 3/2000 |
| WO | WO 2007/048930 A2 | 5/2007 |
| WO | WO-2007/111256 A1 | 10/2007 |

OTHER PUBLICATIONS

International Search Report from counterpart PCT Application No. PCT/FR2010/050161; Report dated May 7, 2010, Published Jan. 27, 2006.

Search Report from counterpart French Application No. 0408031; Report dated Mar. 7, 2011.

Japanese Office Action for related Japanese Application No. 2011-546928; action dated Sep. 3, 2013.

* cited by examiner

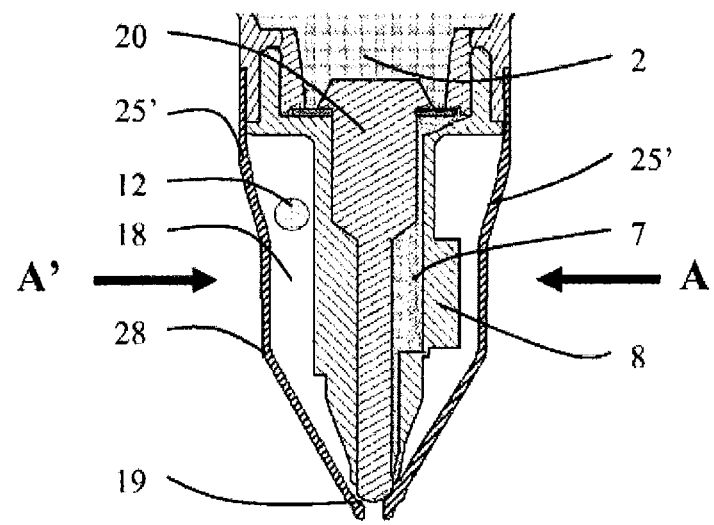
FIG. 10
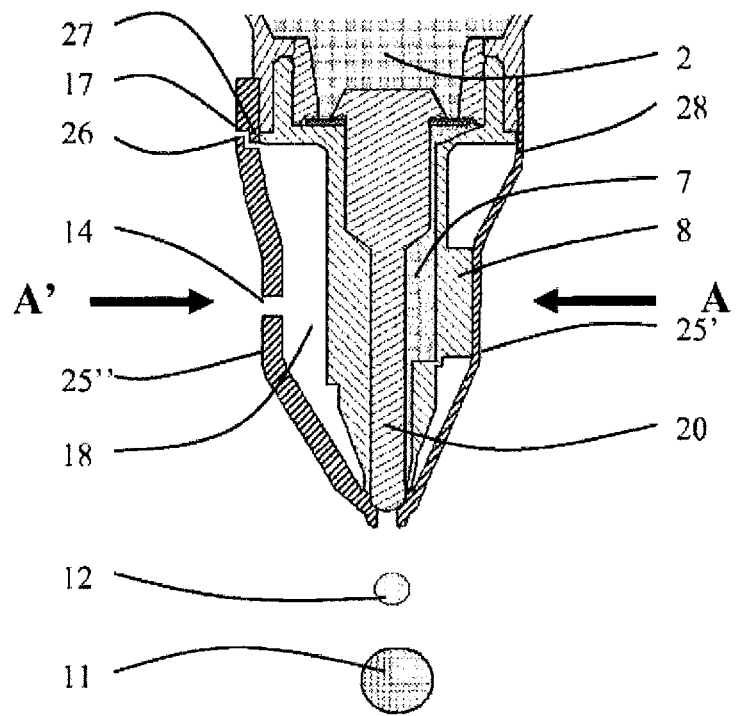
FIG. 11
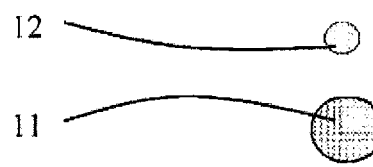

SELF-CLEANING TIP

CROSS-REFERENCE TO RELATED APPLICATIONS

This application is a U.S. national stage filing of International Patent Application No. PCT/FR2010/050161 filed on Feb. 1, 2010, which claims priority under the Paris Convention to French Patent Application No. 09 00433, filed on Feb. 3, 2009.

FIELD OF THE DISCLOSURE

The invention relates to the technical field of packaging, and more particularly to the packaging and dispensing of a liquid or viscous product intended to be kept in clean or sterile conditions without the addition of preservatives, and to be dispensed in portions or in doses, particularly drops.

BACKGROUND OF THE DISCLOSURE

More particularly, the object of the invention is a device for packaging and dispensing a product, comprising a container for containing the product to be dispensed by means of a dispensing accessory fitted to the container and comprising a tip.

There are known packaging devices of conventional structure for storing and dispensing a product in measured doses or drops or in any other form, while maintaining its cleanliness and sterility for the entire period of its use.

These devices are used in the pharmaceutical, cosmetic, and food industries, and some are specifically intended for the field of ophthalmology.

Such known devices are described in patents FR 2 770 495, FR 2 638 428, and FR 2 661 401, in which a container is equipped with a dispensing tip having a bacteriological filtering membrane which sterilizes the product as the product leaves the container.

In these devices, the container comprises a flexible portion which, when manually compressed, causes the product to pass through the bacteriological membrane and exit said container through the tip.

Another type of device which obtains an analogous result is described in patent EP 08 61 128, in which the product is dispensed by means of a pump fitted with a nozzle, and the pump has a bacteriological filter in the air replacement circuit.

Another type of device which obtains an analogous result is described in patents FR 04 08 031 and FR 05 10 907, in which the product is discharged through a flexible nozzle fitted to the container and acting as an accessory. This nozzle opens under the effect of the pressure created by pressure on the walls of the container holding the product or on the nozzle itself, and then closes due to its elasticity. A bacteriological filter is placed at the bottom of the container, where there is an opening for air replacement.

Other devices obtaining a similar result include a pump for dispensing the product, equipped with a nozzle and assembled onto a fluid-tight container not having an air replacement circuit.

All of these devices having a bacteriological filter either for the sterile filtration of the product itself or the sterile filtration of the replacement air, or having no filter or air replacement circuit in the container, make it possible to store the product inside the container in a clean or sterile manner for the duration of its use, and from this point of view can be considered to be effective.

However, the major disadvantage of these devices is that they do not ensure there are no bacteria on the outside of the container, particularly at the tip of the nozzle.

When a measured drop of product has been released by one of the means used in these devices, a fraction of this measured drop, which will be referred to below as the residual drop, remains at the tip of the nozzle.

Experience has shown that, for any device and method used to release a measured drop of product, it is not possible to avoid the formation of a residual drop which remains at the tip of the nozzle until the next use of the device.

The formation and subsequent presence of this residual drop is a major disadvantage because, unlike the product inside the container which can be kept clean or sterile, this residual drop remains in contact with the outside air where it could become contaminated.

The goal of these existing devices, which is to keep clean or sterile the product they contain or distribute, without the use of preservatives, is not achieved because although the product is kept clean or sterile inside the container, it can become contaminated at the tip of the distributor nozzle.

Various solutions have been proposed for solving this problem affecting all existing devices.

In the device described in patent FR 2 770 495 mentioned above, the residual drop is sucked back into the container by the effect of the suction caused by expelling the measured drop, and the recovered drop is sterilized by a sterilizing filter placed in the product dispensing circuit.

This solution is intended to eliminate the residual drop, but is not perfect because the suction created inside the container after the measured drop is expelled is not always sufficient to overcome the resistance of the sterilizing filter to the passage of this residual drop, and the drop therefore may not be sucked back into the container.

Another solution has been proposed for devices such as those described in patent EP 08 61 128. This solution consists of having a metal insert with bactericidal properties, such as silver, placed inside the nozzle where it kills any bacteria contaminating the residual drop.

A similar solution consists of incorporating bactericidal material into the plastic which comes into contact with the residual drop.

Such devices also may allow the residual drop to dry in order to decrease the risk of bacterial contamination.

These solutions are not satisfactory, because their effectiveness is only relative and because there is a risk of metal molecules being released into the product, although these devices were designed to avoid the use of preservatives.

SUMMARY OF THE DISCLOSURE

The goal of the invention is to allow the use of devices for dispensing measured drops of clean or sterile product, without the disadvantage of a risk of bacterial contamination outside said device.

More generally, the purpose of the invention is to overcome the disadvantages of similar known devices and to offer a device which is better suited to the diverse requirements of current usage.

In order to achieve the goal of the invention, the invention proposes a device for packaging and dispensing a generally liquid or viscous product, comprising a container for containing the product to be packaged and dispensed in the form of clean or sterile measured doses or drops by means of a dispensing accessory including a tip, wherein the assembly of container and dispensing accessory comprises a flexible and deformable supplemental chamber, actuated simultaneously with said accessory and either suctioning a residual drop present at the end of said accessory after the dispensing of a measured dose or drop, or blowing said residual drop, or blowing said measured dose or drop without permitting the formation of a residual drop.

Measured doses or drops of clean or sterile product are therefore dispensed by simple pressure on the container, on the accessory, or on the tip which is part of the accessory, with the assurance that no possibly contaminated residual drop will remain at the end of the tip after the measured dose or drop is discharged.

As an example, and as described in a variation in patent FR 04 08 031, the device for storing a product and dispensing it as sterile measured drops comprises a container having an opening for the intake of replacement air and a filter for sterilizing said air when it passes inside said container. The product is stored inside said container and dispensed using an accessory tip, referred to as a nozzle in said patent, fitted to said container. This tip comprises a dosing chamber for defining the volume of the measured drop and which, when compressed, for example by using a push button, allows said drop to be expelled from said container by opening a valve preventing the entry of outside air into the dosing chamber.

Another valve, situated between the dosing chamber and the inside of the container, prevents any return of product from inside the dosing chamber to inside the container when the dosing chamber is compressed, and allows filling said dosing chamber by suctioning product from the container when said dosing chamber is released.

Thus the device of the invention additionally and advantageously comprises a product dosing chamber, supplied with product from the container by a first valve, and placed in communication with outside the device by means of a second valve in order to dispense a measured dose or drop of product, when said accessory is actuated.

The supplemental chamber may be positioned on the outside of the tip.

Advantageously, and in a first embodiment of the invention, a supplemental part is placed on the outside of the tip in which this dosing chamber is located. This supplemental part is made of a preferably flexible and elastic material, and is integrally attached with a fluid-tight seal to the base of said tip which it surrounds. This supplemental part is made and assembled with the tip such that a volume of free space is created between this supplemental part and the tip itself. This free space constitutes the supplemental chamber which is compressed then released automatically when the dosing chamber is compressed then released, which acts to suction the residual drop, or to blow it, or to blow the measured drop while preventing the creation of a residual drop.

In a first variation, the end of the supplemental part comprises an outlet which is cylindrical in shape and is assembled in a fluid-tight manner with the end of the tip on the dosing chamber side and in a non-fluid-tight manner on the side opposite the dosing chamber. When a measured drop is expelled after the dosing chamber and the supplemental chamber are compressed, the residual drop which is created and which remains in the cylindrical outlet of the supplemental part is sucked into the supplemental chamber when the assembly consisting of the dosing chamber and the supplemental chamber is released.

In another embodiment, the portion of the external part situated on the dosing chamber side may not be in direct contact with a pushbutton of the dosing chamber. In other words, the wall of the supplemental chamber may not be in contact with a pushbutton of the dosing chamber. When the device is used, the air contained in the supplemental chamber is therefore expelled before the measured drop itself is expelled. With this delaying effect the device does not expel air at the same time it expels the calibrated drop. Other means of creating a delaying effect can be implemented, such as a difference in thickness in the walls of the supplemental chamber, with the wall opposite the dosing chamber being thinner and therefore more flexible than the wall on the dosing chamber side.

The wall of the supplemental chamber may therefore be thinner than the wall of the dosing chamber, so that the air contained in the supplemental chamber is expelled before the measured drop is expelled from the dosing chamber.

In another variation, the cylindrical end of the supplemental chamber is assembled with the end of the tip in a manner that is fluid-tight both on the dosing chamber side and the side opposite the dosing chamber. The residual drop can therefore be blown outside the tip with no possibility of suctioning it into the supplemental chamber. In this case the dosing chamber must expel the measured drop before the supplemental chamber expels the air serving to blow the residual drop. Various means may be implemented to delay the compression of the supplemental chamber relative to that of the dosing chamber. The wall of the supplemental part situated on the side opposite the dosing chamber may be thicker, and therefore more rigid, than the wall situated on the dosing chamber side. In other words, the wall of the dosing chamber can be thinner than the wall of the supplemental chamber to allow expelling the measured drop from the dosing chamber before expelling the air contained in the supplemental chamber. Similarly, there can be an opening in the supplemental chamber, which cooperates with a stop placed on a portion of the tip in a manner which forces this opening to remain open and prevents any compression of the air contained in the supplemental chamber while the dosing chamber expels the measured drop, then is closed after the measured drop is expelled, which expels the air contained in the supplemental chamber as this chamber is compressed and thus blows the residual drop. The supplemental chamber may therefore comprise an opening for expelling the measured drop from the dosing chamber before the air contained in the supplemental chamber is expelled.

For the supplemental chamber to be refilled with air after the residual drop has been blown by the air previously contained in said supplemental chamber, there can be a second opening in the wall of said supplemental chamber. This second opening is automatically sealed by the pressure from the user's finger when simultaneously pressing against the side of the dosing chamber and the side of the supplemental chamber as he makes use of the device, and is automatically opened when he stops pressing on both sides of the tip, which allows air to enter the supplemental chamber once again. A pushbutton or the wall of the supplemental chamber can therefore comprise at least one opening to allow the entry of replacement air into said supplemental chamber.

In another embodiment, the supplemental chamber which allows either suctioning or blowing the residual drop, is not created by using a supplemental part surrounding the tip, but is situated inside the tip itself.

This embodiment yields the same result as what is obtained by creating a supplemental chamber situated outside the tip, but has the advantage of eliminating the need for a supplemental part.

This supplemental chamber is created opposite the dosing chamber so that it is compressed and released automatically, when the dosing chamber is compressed as the two sides of the tip are pressed to dispense a measured drop then released after this drop is dispensed.

A means is provided to ensure a complete seal between the two chambers in order to avoid any passage of air or product between them.

The means envisioned and described above for using a supplemental chamber outside the tip to suction or blow the residual drop, are identical for an internal supplemental chamber.

If suctioning the residual drop, there is a therefore a passage at the end of the tip to allow expelling the air contained in the supplemental chamber and then suctioning the residual drop into said supplemental chamber. Similarly, the thicknesses of the walls of the two chambers are different, which has a delaying effect so that the air contained in the supplemental chamber is expelled before the measured drop.

If blowing the residual drop, the elimination of this passage prevents the product from being suctioned into the supplemental chamber, and differences in thickness between the walls of the two chambers achieves a delaying effect so that the measured drop can be dispensed before the air contained in the supplemental chamber expels the residual drop.

In the same manner, the supplemental chamber can have an opening which is only sealed after a certain amount of compression of said chamber, to allow sufficient time for the measured drop to be expelled from the dosing chamber before the air used to blow the residual drop is expelled from the supplemental chamber.

There may also be a second opening in this variation, to allow the supplemental chamber to fill with air after the residual drop is blown, when said chamber is located inside the tip.

The creation of a supplemental chamber in addition to the dosing chamber, regardless of whether the supplemental chamber is located inside or outside the tip, associated with a means for suctioning or blowing the residual drop without interfering with the dispensing of the measured drop, advantageously and in a simple manner prevents a residual drop from remaining at the end of the tip where it is likely to become contaminated.

Tate's Law tells us that the fall of a measured drop depends on its mass and on the diameter of the opening at the end where it forms. For a given diameter of the opening, the measured drop falls once it reaches a mass which is described as the critical mass. In the device of the invention, and in the case of the variation described above which blows the residual drop, it may be advantageous to have a dosing chamber having dimensions that create a measured drop of a mass less than this critical mass, so that the drop does not fall off by itself. It is then the measured drop itself which will be blown without any formation of a residual drop.

This results in a simple device for dispensing sterile measured drops, without leaving a residual drop at the end of the tip which could be contaminated by the outside environment.

BRIEF DESCRIPTION OF THE DRAWINGS

Other features and advantages of the invention will become apparent from the following description with reference to the attached drawings, which represent non-limiting examples of some embodiments and implementations of the object of the invention. In these drawings:

FIG. 10 is a schematic axial cross-sectional view of the device of the invention, representing a tip which is part of the assembly represented in FIG. 1, surrounded by a flexible and deformable part, and FIG. 11 is a view analogous to FIG. 10, with two openings in the flexible and deformable part surrounding the tip, as well as differences in thickness in the walls forming this flexible and deformable part.

Identical numeric references indicate analogous elements in the various embodiments represented and described in the different figures.

DETAILED DESCRIPTION OF THE DISCLOSURE

Figure 1:
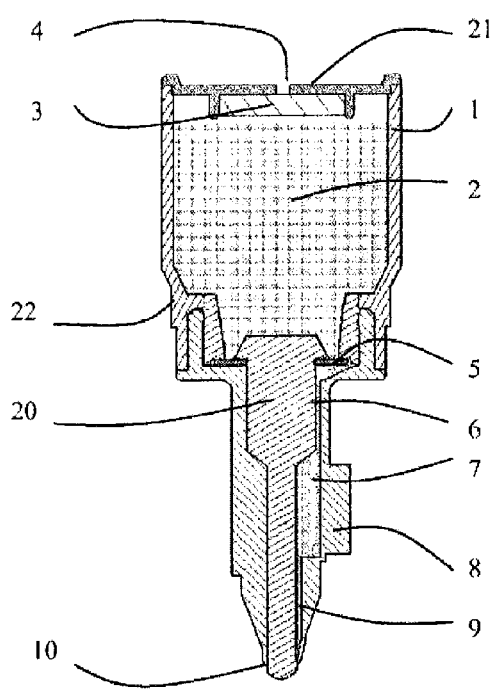
FIG. 1 is a schematic axial cross-sectional view of a variation of the device described in patent FR 04 08 031, representing a container fitted with a dispensing accessory for replacing air through a sterile filter and an accessory tip, referred to as a nozzle in said patent, comprising a dosing chamber and two valves for dispensing measured drops.

As represented in FIG. 1, the packaging and dispensing device described in patent FR 04 08 031 comprises a container 1, consisting of a bottom 21 which has an air replacement and filtration assembly comprising a passage 4 for air intake leading to an air filter 3, and an upper end 22 integrally attached to a tip 20 which has a dosing chamber 7, actuated by a pushbutton 8 and surrounded by two valves 5 and 10 as well as two supply channels 6 and 9 for dispensing the product 2 contained in the body of the container 1.

The first valve 10 allows product 2 contained in the dosing chamber 7 to travel through the channel 9 towards the outside when said chamber is compressed by pressing on the pushbutton 8, without the outside air being able to enter into said dosing chamber 7 when said pushbutton 8 is released; the second valve 5 allows product 2 contained in the container 1 to enter the dosing chamber 7 through the channel 6 when the pushbutton is released, without the product 2 contained in the dosing chamber 7 being able to return into the container 1 when said chamber is compressed.

Figure 2:
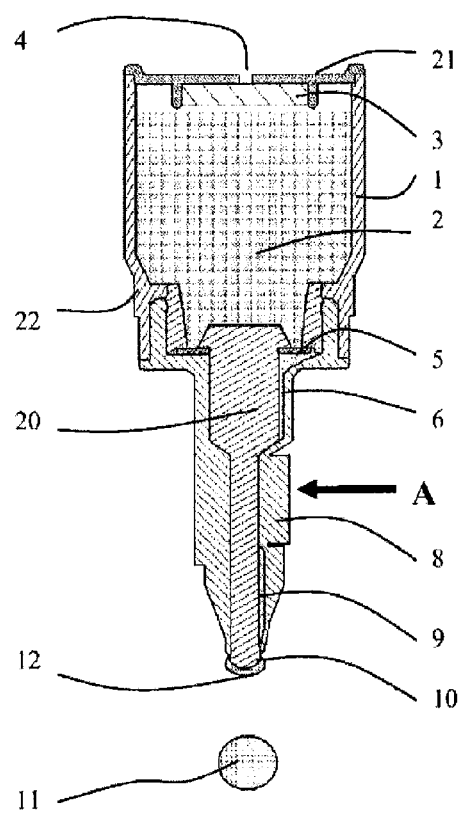
FIG. 2 is an axial cross-sectional view of the device represented in FIG. 1 after forces are applied to a measured drop and it is expelled with formation of a residual drop.

FIG. 2 represents this same device when forces are applied to it by pressure on the pushbutton 8 in the direction of the arrow A, causing compression of the dosing chamber 7, the expelling of a measured drop 11 through the valve 10, and formation of a residual drop 12.

Figure 3:
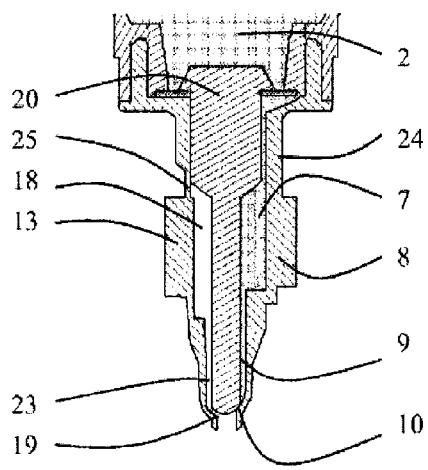
FIG. 3 is a schematic axial cross-sectional view of the dispensing accessory of the invention, in which a tip is represented which is part of the assembly represented in FIG. 1, having a supplemental chamber situated inside the tip itself as well as an open channel at its end.

FIG. 3 represents the tip 20 with a supplemental chamber 18 inside it and opposite the dosing chamber 7, separated from the dosing chamber by a fluid-tight means preventing any passage between them, and actuated by a pushbutton 13, as well as a channel 23 open at its end 19. The wall 24 of the dosing chamber is thicker than the wall 25 of the supplemental chamber 18; when forces are applied to the device by simultaneously pressing on the pushbuttons 8 and 13, the supplemental chamber is compressed before the dosing chamber.

Figure 4:
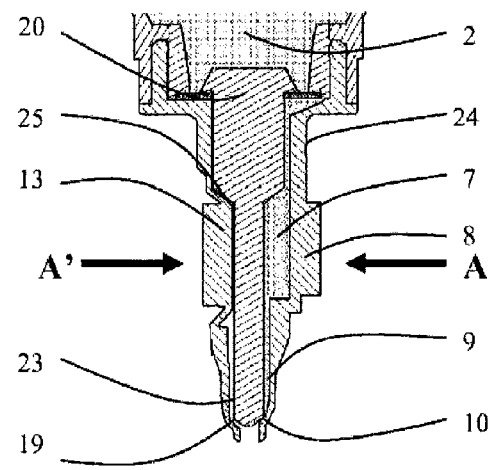
FIG. 4 is a view analogous to FIG. 3 when forces are applied to the device and only the supplemental chamber has been compressed.
Figure 5:
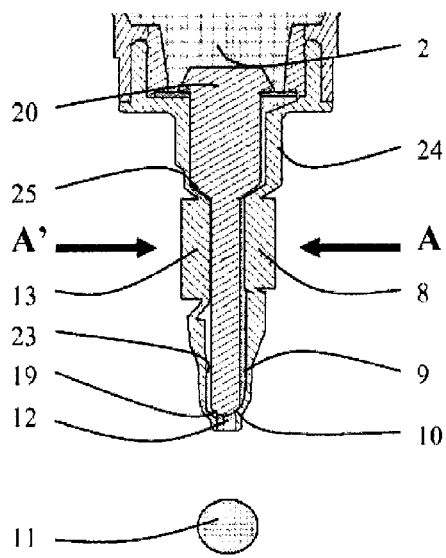
FIG. 5 is a view analogous to FIG. 4 when forces are applied to the device and the dosing chamber is compressed.
Figure 6:
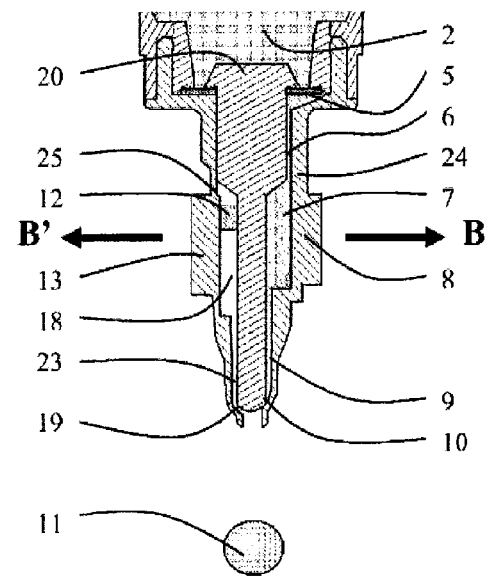
FIG. 6 is a view analogous to FIG. 5 when forces are no longer applied to the device.

Referring to FIGS. 4, 5, and 6, the device operates in the following manner:

Simultaneous manual pressure by a user on pushbuttons 8 and 13, in the direction of arrows A and A', first causes (FIG. 4) the compression of the supplemental chamber 18, as the wall 25 of this supplemental chamber 18 is thinner and therefore less resistant to stresses than the wall 24 of the dosing chamber 7 which is not yet compressed.

This earlier compression of the supplemental chamber 18, preceding that of the dosing chamber 7, has the effect of expelling the air contained in this supplemental chamber 18 through the channel 23 and its open end 19, before expelling a measured drop 11 of product 2, in a manner that does not expel a mixture of air and product.

Next (FIG. 5), simultaneous pressure on the pushbuttons 8 and 13 will cause compression of the dosing chamber 7 and the expelling of a measured drop 11 of product 2 through the channel 9 and the opening of the valve 10 as well as the formation of a residual drop 12.

Thirdly (FIG. 6), the release of pressure by the user in the direction of the arrows B and B', and the return of the chambers 7 and 18 to their initial shapes, causes the dosing chamber 7 to refill with product 2 as the valve 5 opens, with the product traveling through the channel 6 without any outside air allowed to enter said dosing chamber because the valve 10 is elastically closed. This also causes the supplemental chamber 18 to suction in the residual drop 12 through the open end 19 and the channel 23.

The communication between the supplemental chamber 18 and the outside air, through the channel 23 and the open end 19, results in drying up the residual drop previously suctioned into said chamber 18.

Because of this suctioning and drying, the residual drop completely disappears from the end of the tip.

With respect to the above-described dispensing device, it may be appreciated by those skilled in the art that the tip 20, as particularly described in reference to FIGS. 3-6, is situated below the container 1 (shown only in FIGS. 1 and 2). By way of nomenclature, the tip 20 along with all of its associated "dispensing" parts, including the valve 5, the valve 10, the dosing chamber 7, and the supplemental chamber 18, are herein collectively called a "dispensing accessory". The latter term is herein defined to also include the dispenser "push" buttons 8 and 13 associated with respective dosing and supplemental chambers 7, 18.

Figure 7:
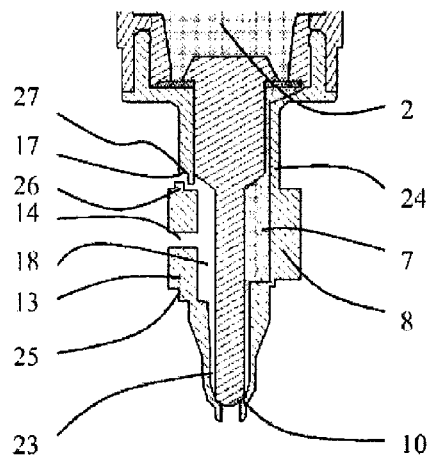
FIG. 7 is a view analogous to FIG. 3, showing a supplemental chamber with two openings and a channel closed at its end.

FIG. 7 represents a variation of the device, in which the end of the channel 23 of the supplemental chamber 18 is closed and the wall 25 of the supplemental chamber 18 is thicker than the wall 24 of the dosing chamber 7.

Simultaneous manual pressure by a user on the pushbuttons 8 and 13 in the direction of arrows A and A' (FIG. 8) therefore first compresses the dosing chamber 7 which has the thinnest wall and so is the least resistant to stresses, causing a measured drop 11 of product 2 to exit through the channel 9 and the valve 10, and the formation of a residual drop 12, before the compression of the supplemental chamber 18 which has the thickest wall 25 and so is the most resistant to stresses, expelling the air it contains.

Expelling the measured drop 11 prior to expelling the air contained in the supplemental chamber 18 is necessary to avoid expelling a mixture of air and product 2. This earlier release of the measured drop 11 of product 2 can be obtained by means other than differences in thickness between the walls of the two chambers.

Figure 7A:
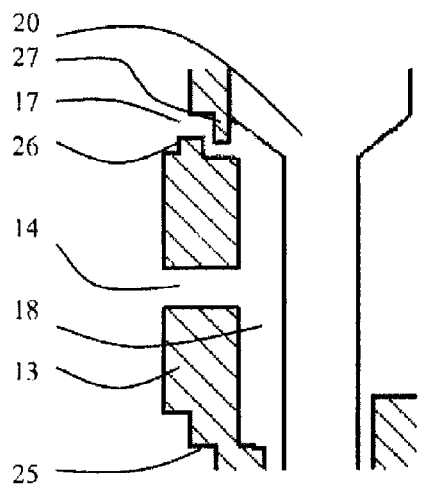
FIG. 7a is an enlarged view of the portion of FIG. 7 showing the two openings.

FIGS. 7 and 7a show an opening 17 in the wall 25 of the supplemental chamber 18, as well as a lip 26 cooperating with another lip 27. This opening 17 (FIG. 7a) is open when forces are not being applied to the device. When a user presses simultaneously on the pushbuttons 8 and 13, which has the effect of compressing the two chambers 7 and 18, the air contained in the supplemental chamber 18 escapes through the opening 17 until the two lips 26 and 27 come in contact with each other and close off said opening 17. During this period of time the chamber 7 is compressed and a measured drop 11 of product 2 is expelled.

This supplemental means prevents air from the supplemental chamber 18 being expelled at the same time as the measured drop 11 of product 2.

Figure 8:
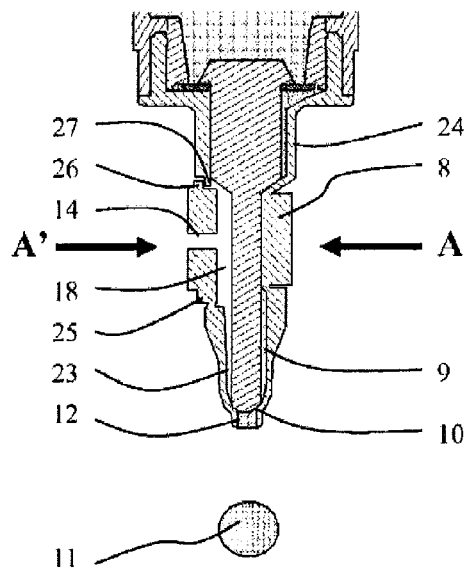
FIG. 8 is a view analogous to FIG. 7 when forces are applied to the device and only the dosing chamber is compressed.

FIG. 8 represents the device in a position where action by a user on the pushbuttons 8 and 13 in the direction of the arrows A and A' compresses the dosing chamber 7 and expels a measured drop 11, while the pushbutton 13 advances and the opening 17 starts to be sealed off by the contact between the two lips 26 and 27 without the supplemental chamber yet being compressed.

The presence of the opening 17 and its delayed closure by the cooperating lips 26 and 27 prevents any compression of the supplemental chamber 18 while the measured drop is expelled and also prevents any expelling of a mixture of air and product 2.

Figure 9:
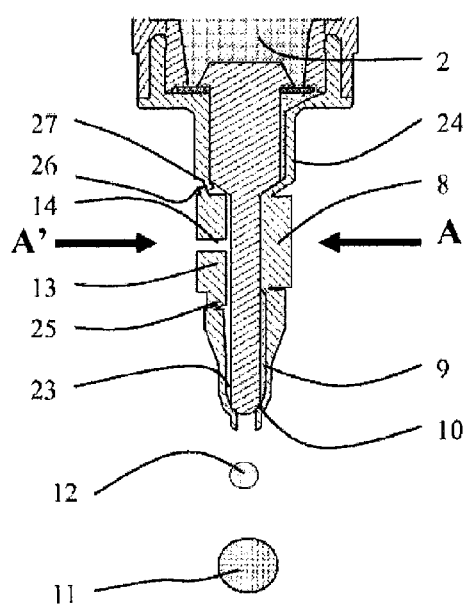
FIG. 9 is a view analogous to FIG. 8 when forces are applied to the device and the supplemental chamber is compressed.

FIG. 9 shows the device when the user continues to apply forces to it by pressing on the pushbuttons 8 and 13; the supplemental chamber 18 is compressed but its opening 17 for allowing air to escape is sealed, which expels the air through the channel 23, opens the valve 10, and blows away the residual drop 12.

If the mass of the measured drop 11, determined by the volume of the dosing chamber 7, is less than the critical mass according to Tate's law, the measured drop 11 does not fall by itself, but remains attached to the end of the tip 2 and is combined with the residual drop 12.

Then when the supplemental chamber 18 is compressed after the opening 17 is closed, it is the measured drop 11 which is blown without any formation of a residual drop 12.

A hole 14 is provided (FIGS. 7 and 7a) to allow the supplemental chamber 18 to refill with air. It is closed off by the user's finger when the user exerts pressure on the pushbutton 13 in the direction of the arrow A' (FIGS. 8 and 9), and is opened when the user releases the pressure.

FIG. 10 represents the tip 20 surrounded by a flexible external part 28 forming a supplemental chamber 18 opposite the dosing chamber 7. The wall 25' of the external part 28 is not in contact with the pushbutton 8 and the inside of said supplemental chamber is connected to the outside air by means of the channel 19.

The device represented is in accordance with the invention and functions identically to the device represented in FIG. 3, in which the supplemental chamber 18 is situated inside the tip.

When forces are applied to the device and a user exerts pressure on the walls of the flexible part in the direction of the arrows A and A', because the wall 25' is not in contact with the pushbutton 8 the air contained in the supplemental chamber 18 is expelled before the dosing chamber 7 is itself compressed by the pressure of the wall 25' on the pushbutton 8 and a measured drop 11 is expelled. This prevents any expelling of air at the same time as the product 2.

When the user releases his pressure, the supplemental chamber resumes its shape and suctions the residual drop 12 which forms after the measured drop 11 is expelled, under the same conditions as the device represented in FIG. 6.

FIG. 11 represents a device comprising a tip 20 surrounded by an external flexible part 28. The wall 25' of said part is in contact with the pushbutton 8 but is thinner than the opposite wall 25" which has two openings 17 and 14.

This device functions identically to the one represented in FIGS. 7, 8 and 9, and blows either the residual drop after expelling a measured drop, or the measured drop itself without any formation of a residual drop when its mass has been chosen so that it does not fall off on its own.

The same delayed effect of compression on the supplemental chamber 18 compared to compression on the dosing chamber 7 is obtained by means identical to those described for FIGS. 7, 7a, 8 and 9, and the hole 14 allows the supplemental chamber 18 to refill with air under the same conditions.

Other embodiments of the supplemental chamber associated with the tip are possible without leaving the scope of the invention, if this chamber has the function of suctioning the residual drop or blowing the residual drop or blowing the measured drop without allowing the formation of a residual drop.

Other analogous means may also be implemented, without leaving the scope of the invention, to prevent any simultaneous expelling of air from the supplemental chamber and of product from the dosing chamber.

The invention claimed is:

1. A device for packaging and dispensing a generally liquid or viscous product, intended to be kept in clean or sterile conditions comprising a container for containing the product to be packaged and dispensed in the form of clean or sterile measured doses or drops by means of a dispensing accessory including a tip, wherein said container and said dispensing accessory constitute an assembly, wherein said assembly comprises;
   a product dosing chamber, supplied with product from the container by a first valve, and providing passage to outside the dispensing accessory by means of a second valve in order to dispense a measured dose or drop of product, when said accessory is actuated,
   a flexible and deformable supplemental chamber, actuated simultaneously with said dosing chamber and either suctioning a residual drop present at the end of said accessory after the dispensing of a measured dose or drop, or blowing said residual drop, or blowing said measured dose or drop without permitting the formation of a residual drop, said flexible and deformable supplemental chamber comprising a channel open at its end to the outside, near said second valve of the dispensing accessory,
   said flexible and deformable supplemental chamber and said product dosing chamber being separated by fluid tight means preventing any passage between them,
wherein said supplemental chamber is situated inside the dispensing accessory, wherein the wall of the supplemental chamber is thinner than the wall of the dosing chamber such that air contained in the supplemental chamber is expelled before the measured drop is expelled from the dosing chamber.

2. A device for packaging and dispensing a generally liquid or viscous product, intended to be kept in clean or sterile conditions comprising a container for containing the product to be packaged and dispensed in the form of clean or sterile measured doses or drops by means of a dispensing accessory including a tip, wherein said container and said dispensing accessory constitute an assembly, wherein said assembly comprises:
   a product dosing chamber, supplied with product from the container by a first valve, and providing passage to outside the dispensing accessory by means of a second valve in order to dispense a measured dose or drop of product, when said accessory is actuated,
   a flexible and deformable supplemental chamber, actuated simultaneously with said dosing chamber and either suctioning a residual drop present at the end of said accessory after the dispensing of a measured dose or drop, or blowing said residual drop, or blowing said measured dose or drop without permitting the formation of a residual drop, said flexible and deformable supplemental chamber comprising a channel open at its end to the outside, near said second valve of the dispensing accessory,
   said flexible and deformable supplemental chamber and said product dosing chamber being separated by fluid tight means preventing any passage between them,
wherein said supplemental chamber is situated inside the dispensing accessory, wherein the wall of the dosing chamber is thinner than the wall of the supplemental chamber such that the measured drop is expelled from the dosing chamber before air contained in the supplemental chamber is expelled.

3. The device according to claim 2, wherein a pushbutton or the wall of the supplemental chamber comprises at least one opening to allow the intake of replacement air into said chamber.

4. A device for packaging and dispensing a generally liquid or viscous product, intended to be kept in clean or sterile conditions comprising a container for containing the product to be packaged and dispensed in the form of clean or sterile measured doses or drops by means of a dispensing accessory including a tip, wherein said container and said dispensing accessory constitute an assembly, wherein said assembly comprises:
   a product dosing chamber, supplied with product from the container by a first valve, and providing passage to outside the dispensing accessory by means of a second valve in order to dispense a measured dose or drop of product, when said accessory is actuated,
   a flexible and deformable supplemental chamber, actuated simultaneously with said dosing chamber and either suctioning a residual drop present at the end of said accessory after the dispensing of a measured dose or drop, or blowing said residual drop, or blowing said measured dose or drop without permitting the formation of a residual drop, said flexible and deformable supplemental chamber comprising a channel open at its end to the outside, near said second valve of the dispensing accessory,
   said flexible and deformable supplemental chamber and said product dosing chamber being separated by fluid tight means preventing any passage between them,
wherein said supplemental chamber is situated inside the dispensing accessory, wherein the supplemental chamber comprises an opening such that the measured drop is expelled from the dosing chamber before air contained in the supplemental chamber is expelled.

5. A device for packaging and dispensing a generally liquid or viscous product, intended to be kept in clean or sterile conditions comprising a container for containing the product to be packaged and dispensed in the form of clean or sterile measured doses or drops by means of a dispensing accessory including a tip, wherein said container and said dispensing accessory constitute an assembly, wherein said assembly comprises:
- a product dosing chamber, supplied with product from the container by a first valve, and providing passage to outside the dispensing accessory by means of a second valve in order to dispense a measured dose or drop of product, when said accessory is actuated,
- a flexible and deformable supplemental chamber, actuated simultaneously with said dosing chamber and either suctioning a residual drop present at the end of said accessory after the dispensing of a measured dose or drop, or blowing said residual drop, or blowing said measured dose or drop without permitting the formation of a residual drop, said flexible and deformable supplemental chamber comprising a channel open at its end to the outside, near said second valve of the dispensing accessory,
- said flexible and deformable supplemental chamber and said product dosing chamber being separated by fluid tight means preventing any passage between them, wherein said supplemental chamber is situated outside the tip, wherein a wall of said dosing chamber is thinner than a wall of said supplemental chamber such that a measured drop is expelled from said dosing chamber before air contained in said supplemental chamber is expelled.

6. The device according to claim 5, wherein a pushbutton or a wall of said supplemental chamber comprises at least one opening to allow intake of replacement air into said supplemental chamber.

7. A device for packaging and dispensing a generally liquid or viscous product, intended to be kept in clean or sterile conditions comprising a container for containing the product to be packaged and dispensed in the form of clean or sterile measured doses or drops by means of a dispensing accessory including a tip, wherein said container and said dispensing accessory constitute an assembly, wherein said assembly comprises:
- a product dosing chamber, supplied with product from the container by a first valve, and providing passage to outside the dispensing accessory by means of a second valve in order to dispense a measured dose or drop of product, when said accessory is actuated,
- a flexible and deformable supplemental chamber, actuated simultaneously with said dosing chamber and either suctioning a residual drop present at the end of said accessory after the dispensing of a measured dose or drop, or blowing said residual drop, or blowing said measured dose or drop without permitting the formation of a residual drop, said flexible and deformable supplemental chamber comprising a channel open at its end to the outside, near said second valve of the dispensing accessory,
- said flexible and deformable supplemental chamber and said product dosing chamber being separated by fluid tight means preventing any passage between them, wherein said supplemental chamber is situated outside the tip, wherein said supplemental chamber comprises an opening such that a measured drop is expelled from said dosing chamber before air contained in said supplemental chamber is expelled.

\* \* \* \* \*